US005620897A

United States Patent [19]

Zappe

[11] Patent Number: 5,620,897
[45] Date of Patent: Apr. 15, 1997

[54] AUTOMATED METHOD AND TEST KIT FOR FREE FATTY ACIDS IN COOKING FATS AND OILS

[76] Inventor: Ronald J. Zappe, 326 Woodstone Dr., Baton Rouge, La. 70808

[21] Appl. No.: 562,469

[22] Filed: Nov. 24, 1995

[51] Int. Cl.$^6$ .................................................. G01N 33/06
[52] U.S. Cl. .......................... 436/23; 422/68.1; 422/74; 422/102; 436/20; 436/22; 436/71; 206/569; 426/417; 426/231
[58] Field of Search ...................... 422/68.1, 102, 422/74; 436/20, 22, 23, 71; 206/569; 426/417, 231

[56] References Cited

U.S. PATENT DOCUMENTS

| | | | |
|---|---|---|---|
| 169,727 | 11/1875 | Peters | 436/20 |
| 270,489 | 1/1883 | Schubert | 422/102 |
| 294,052 | 2/1884 | Lactometer | 436/23 |
| 437,356 | 9/1890 | Clement | 436/22 |
| 602,780 | 4/1898 | Stokes | 422/74 |
| 710,553 | 10/1902 | Anderson | 422/74 |
| 749,343 | 1/1904 | Vogtherr | 436/22 |
| 1,158,275 | 10/1915 | Phillips | 422/74 |
| 1,428,020 | 9/1922 | Farrington | 422/74 |
| 1,907,103 | 5/1933 | Harris | 436/71 |
| 2,129,516 | 9/1938 | Wood | 436/23 |
| 3,045,495 | 7/1962 | Spencer et al. | 422/102 |
| 3,615,226 | 10/1971 | Apter | 436/20 |
| 4,654,309 | 3/1987 | Mlinar et al. | 436/20 |

*Primary Examiner*—Jill Warden
*Assistant Examiner*—Sharidan Carrillo
*Attorney, Agent, or Firm*—Reginald F. Roberts, Jr.

[57] ABSTRACT

Apparatus and method for determining the percentage of free fatty acids in cooking fats and oils. A kit for this analysis includes a test cylinder calibrated for (a) volume of test sample, (b) volume of acid-base indicator solution, and (c) a set of lines marked to be read directly as the percentage of free fatty acids in the sample.

3 Claims, 1 Drawing Sheet

AUTOMATED METHOD AND TEST KIT FOR FREE FATTY ACIDS IN COOKING FATS AND OILS

BACKGROUND OF THE INVENTION

The present invention relates to chemical analysis. More particularly, the present invention relates to the determination of fatty acids in cooking fats and oils.

The manufacturers of cooking fats and oils recommend a maximum level of three to four percent (3–4%) free fatty acids in cooking oils. The term "free fatty acids" is used to distinguish fatty acids which are not chemically bound to glycerol moities as carboxylic esters. Fats and oils, when pure, consist almost entirely of the esters of fatty acids and glycerol. Those which are solid at room temperature are commonly referred to as "fats," and those liquid at room temperature as "oils."

As fats and oils are used in cooking, they tend to break down, degrade, and hydrolyze to free fatty acids, glycerol, and other polar materials. The free fatty acids are among the harmful products of this degradation. Many restaurants continue to use their cooking fats and oils well beyond the 3–4% recommended maximum. This is primarily because there is no accurate method for determining the percentage of free fatty acids in cooking fats and oils which is simple and quick. One method currently available is the American Oil Chemists Society (AOCS) Procedure CA5a-40, which is the standard procedure used in and by the laboratories. This procedure is summarized as follows, with milliliter(s) abbreviated as "ml", normality as "N", sodium hydroxide as "NaOH", and percent as "%".

A numerical table is used to determine the sample weight; the volume of 95% and 5% water by volume ethyl alcohol "neutralized" with alkali to a faint, permanent pink color; and the concentration of standard sodium hydroxide solution which are to be used in the test.

The designated sample size is weighed into an oil sample bottle or Erlenmeyer flask.

The specified volume of 95% hot "neutralized" ethyl alcohol and 2 ml of a 1% by weight solution of phenolphthalein in 95% ethyl alcohol are added.

The sample is then titrated with the specified concentration of aqueous sodium hydroxide, shaking vigorously until the appearance of the first permanent pink color of the same intensity as that of the 95% alcohol before the addition of the sample, "permanent" being defined as persisting for 30 seconds.

The percentage of free fatty acids, expressed usually as oleic acid, is then calculated, using the following formula:

$$\% \text{ Fatty Acid} = \frac{\text{ml NaOH} \times \text{N} \times 28.2}{\text{grams of sample}}$$

Clearly, the above method is time-consuming and requires apparatus not generally available to restaurants. What is needed is a test procedure which is reliable, accurate, simple, quick, and inexpensive. The present invention provides the apparatus and method for such a test procedure.

SUMMARY OF THE INVENTION

In general, the present invention in a first aspect provides an automated analytical method for determining the concentration of a constituent in a sample by titrating the constituent with a reagent known to quantify the concentration of the constituent in the sample. The method comprises (a) calibrating and marking a container with a first mark indicating the level to which the container is to be filled with the sample and a solution of a visual indicator, and (b) calibrating and marking the container with a plurality of second marks disposed above the first mark. Each of the second marks indicates the volume of the reagent required to reach the equivalence point of the titration, and is so labeled as to be read directly as the percentage of the constituent in the sample. The method further comprises (c) adding the sample mixed with the indicator solution to the container up to the level indicated by the first mark; (d) admixing the reagent to and with the sample until the equivalence point has been reached, as determined by a change in color of the indicator; and (e) reading the percentage of the constituent directly from the second mark which indicates the volume of the reagent that was required to reach the equivalence point of the titration. The term "admixing" is used to mean "adding while mixing."

In a second aspect the invention provides an automated method for determining the concentration of free fatty acids in a sample of cooking fat or oil. The method comprises (a) calibrating and marking a container with a first mark indicating the level to which the container is to be filled with the liquid sample of cooking fat or oil, (b) calibrating and marking the container with a second mark disposed above the first mark, (c) calibrating and marking the container with a plurality of third marks disposed above the second mark and so labeled as to be read directly as the percentage of fatty acids in the sample, (d) filling the container to the level indicated by the first mark with a hot sample of the cooking fat or oil, (e) admixing an alcoholic solution of a visual acid-base indicator to and with the sample up to the level indicated by the second mark, (f) titrating the fatty acids by slowly admixing a standard solution of an alkali-metal hydroxide to and with the contents of the container until the indicator indicates that the equivalence point of the titration has been reached, and (g) reading the percentage of free fatty acids in the cooking fat or oil directly from the third mark which indicates the volume of the standard solution of the alkali-metal hydroxide required to reach the equivalence point of the titration.

In a third aspect the present invention provides apparatus for automatedly determining the concentration of a constituent in a sample by titrating the constituent with a reagent known to quantify the concentration of the constituent in the sample. The apparatus comprises a container calibrated and marked with (a) a first mark indicating the level to which the container is to be filled with the sample mixed with a solution of an indicator, and (b) a plurality of second marks indicating the volume of the reagent required to reach the equivalence point of the titration. The second marks are disposed above the first mark, and are so labeled as to be read directly as the percentage of the constituent in the sample.

In a fourth aspect the invention provides apparatus for automatedly determining the concentration of free fatty acids in cooking fats and oils. The apparatus comprises a container calibrated and marked with (a) a first mark indicating the level to which the container is to be filled with the fat or oil sample, (b) a second mark disposed above the first mark, and (c) a plurality of third marks disposed above the second mark. The second mark indicates the liquid level in the container after a solution of an acid-base indicator has been added to the sample. Each of the third marks indicates the liquid level in the container after the sample has been titrated to the equivalence point with a reagent which quantifies the concentration of fatty acids in the sample of cooking fat or oil, and is so labeled as to be read directly as the percentage of the free fatty acids in the cooking oil.

DETAILED DESCRIPTION OF THE INVENTION

Figure 1:
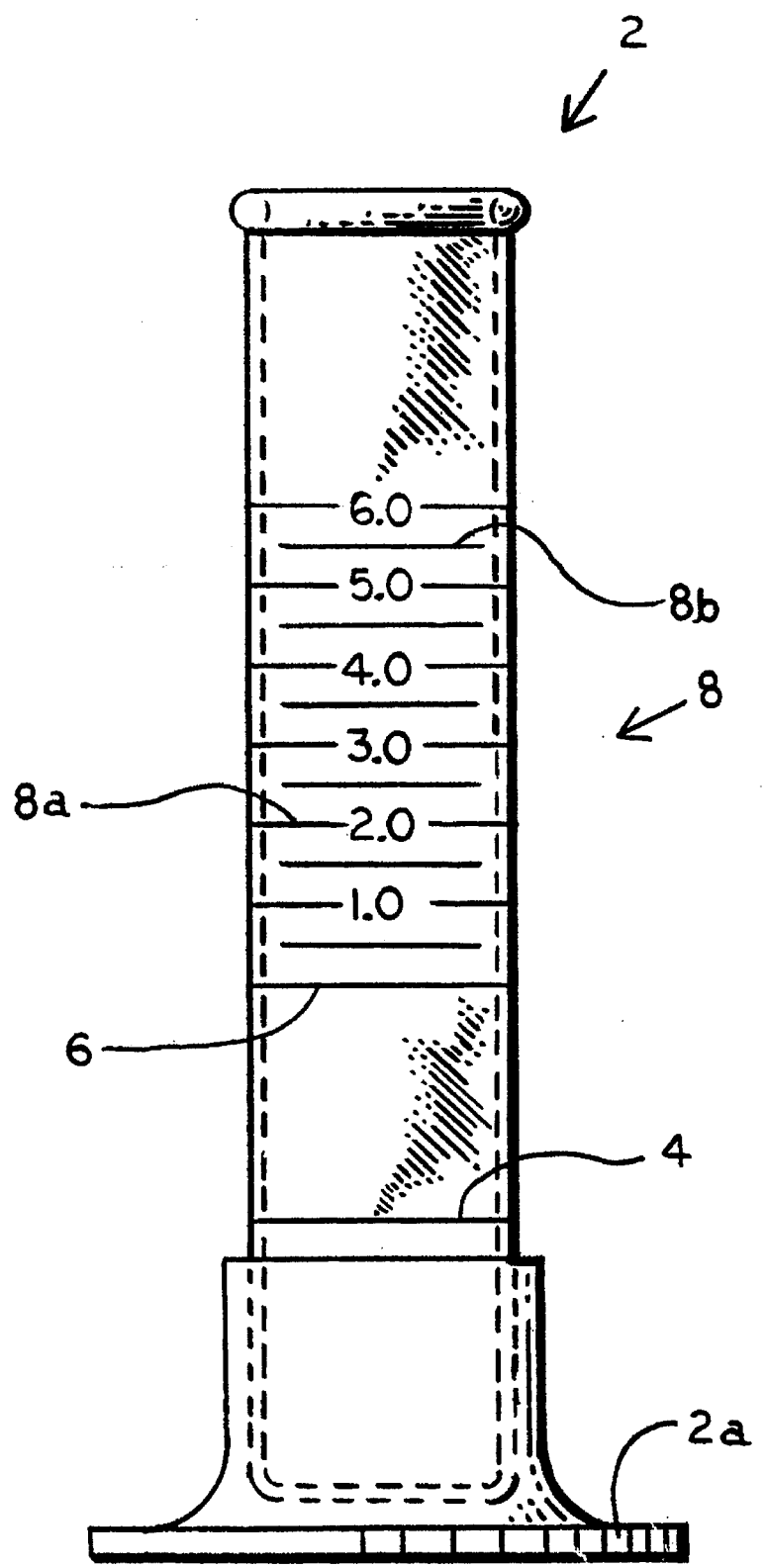
FIG. 1 is a schematic representation of a test cylinder made in accordance with the principles of the present invention.

More specifically, reference is made to FIG. 1, in which is shown a test cylinder made in accordance with the principles of the present invention, and generally designated by the numeral 2.

The test cylinder 2 is a transparent vessel having inscribed thereon a first line 4, a second line 6, and a plurality of third lines 8. Some of the lines 8 are labeled with numerical indicia and are designated by the numeral 8a; others are unlabeled and are designated by the numeral 8b. The lines 8a are somewhat longer than the lines 8b. The test cylinder 2 beneficially includes a detachable plastic base 2a for stabilization.

A hot sample of the cooking fat or oil to be analyzed is poured directly from a fryer into the test cylinder 2 up to the level indicated by the first line 4. Alternatively, the hot sample may be transferred first to a beaker (not shown) and shortly or immediately thereafter into the test cylinder 2 up to the first line 4. A dilute solution of phenolphthalein alcohol containing a small amount of water and a trace amount of an alkali-metal hydroxide is then admixed to and with the oil sample up to the level indicated by the second line 6. The sample is then titrated with a standard solution, preferably in water, of sodium or potassium hydroxide to the phenolphthalein endpoint, indicated by the persistence of a pink color for thirty seconds. The percentage of free fatty acids, expressed as oleic acid, in the sample is then read directly from the third line 8 which indicates the liquid level in the test cylinder 2 after the titration has been completed. In most instances, for a precise readout of a level between two of the lines 8, the percentage is found by interpolation.

Instead of filling the test cylinder 2 up to the first line 4 with the sample and up to the second line 6 with the indicator solution, the sample and indicator solution can be premixed, using a calibrated container or calibrated containers for measuring the volume of the sample and the indicator solution, before transferring the mixture of sample and indicator solution to the test cylinder 2. The rest of the test procedure is the same as described above. In either case, the stirring required for mixing the various components may be done manually, mechanically, or electrically.

While not critical, the temperature of the fat or oil as it is poured into the test cylinder 2 is preferably between about 300° and about 350° F. This temperature range ensures that the sample will be liquid, and minimizes changes in the density of the fat or oil as a result of temperature variations.

The concentration of sodium or potassium hydroxide is preferably between about one one-hundredth and one gram equivalent weight (gew) per liter. Even more preferably, the concentration is from about five one-hundredths to about five tenths of a gew per liter. Most preferably, the concentration of the hydroxide is approximately one tenth gew per liter; i.e., about one tenth normal (0.1N).

The concentration of phenolphthalein in the alcoholic solution thereof is preferably from about 0.01 to about 0.04 percent by weight. Even more preferably, the predominantly alcoholic solution of phenolphthalein is prepared by diluting a 0.5% by weight solution of phenolphthalein in 50 % water and 50% alcohol by volume to and with the neat alcohol, and adding 0.1N sodium hydroxide solution to "neutralized" to a pink color. Even more preferably, the solution is prepared by diluting one volume of the concentrated solution of phenolphthalein in 50% alcohol and 50% water with fourteen volumes of alcohol, and adding one drop of 0.1N sodium hydroxide solution for every 14 ml of alcohol. Most preferably, the alcohol is isopropyl alcohol.

For high visibility the lines 4, 6, 8, 8a, and 8b are preferably black. Even more preferably, the lines 8a labeled with numerals extend from about fifty to about seventy percent of the circumference of the test cylinder 2, and the lines 8b not labeled with numerals extend from about twenty-five to about thirty-five percent of the circumference of the cylinder 2.

The size of the cylinder 2 and of the sample can and may vary within wide limits. It is critical, however, that the test cylinder 2 be standardized for a specific sample weight of fat or oil, a specific volume of alcoholic pheonphthalein solution, and a specific concentration of sodium or potassium hydroxide. It has been found that a very satisfactory set of conditions is represented by 14.1+ or −0.1 grams of oil, 15 ml of indicator solution, and 0.1N sodium or potassium hydroxide. For these conditions, optimum dimensions of the test cylinder 2 are about 155 millimeters (mm) in height and about a 30-mm outside diameter (O.D.). Each line 8a then represents 5 ml, and each line 8b 2.5 ml of titrant. The calibrated volume of the cylinder 2 is approximately 60 ml.

The test cylinder 2 is preferably made of glass. Even more preferably, the cylinder 2 is made of clear, colorless glass. Most preferably the test cylinder 2 is made of borosilicate glass which is commercially available under the trademark "KIMAX", a registered trademark of the Kimble Glass Company, Vineland, N.J.

Apparatus and directions for carrying out analyses for free fatty acids in cooking fat or oil in accordance with the principles of the present invention are beneficially made available as test kits. Each test kit includes (a) stock solutions of alcoholic phenolphthalein solution and 0.1N aqueous sodium hydroxide solution, (b) four-ounce fill bottles for the phenolphthalein and sodium hydroxide solutions, (c) a graduated 30 ml KIMAX dropper, and (d) the calibrated test cylinder 2. The test kit also includes a stirring rod, a pair of safety eyeglasses, and a set of instructions.

While the detailed description of the present invention has been limited to the determination of free fatty acids in cooking fats and oils, it will be apparent to those skilled in the art that the basic method and apparatus are applicable to many other types of analytical determinations.

The invention will now be illustrated by the following examples, which are to be understood as illustrative only, and which are not to be construed as in any way limiting the scope of the invention.

EXAMPLE I

A hot (300°–350° F.) sample of molten lard was poured into the test cylinder 2 up to the level of the first line 4. A solution of about 0.03% by weight of phenolphthalein and of about $3 \times 10^{-4}$ gram equivalent weight of sodium hydroxide per liter in a solvent comprising about 97% isopropyl alcohol and about 3% water by volume was admixed with the lard sample, using a stirring rod to stir and mix the components, up to the second line 6. A water solution of 0.1N sodium hydroxide solution was then used to titrate the sample for free fatty acids, again using the stirring rod to stir the contents of the test cylinder 2 while slowly adding the solution of sodium hydroxide thereto. At the phenolphthalein endpoint, indicated by the persistence of a pink color for thirty seconds, the concentration of fatty acids, expressed as oleic acid, in the lard sample was found by interpolation to be 0.22% by weight.

EXAMPLE II

Using the same procedure as in EXAMPLE I, a hot (300°–350° F.) sample of mixed vegetable oil was titrated to the phenolphthalein endpoint with 0.1N sodium hydroxide solution, and the concentration of free fatty acids in the sample was determined by interpolation to be 1.36% by weight.

EXAMPLE III

Using the same procedure as in EXAMPLE I, a hot 300°–350° F.) sample of molten lard was titrated to the phenolphthalein endpoint with 0.1N sodium hydroxide solution, and the concentration of free fatty acids was determined by interpolation to be 3.20% by weight.

While certain particular details and embodiments have been described in order to illustrate the present invention, it will be apparent to those skilled in the art that many modifications can and may be made therein without departing from the basic concept, spirit, and scope of the invention. For example, the step of adding an alcoholic solution of phenolphthalein could be eliminated by using a standard alcoholic solution of sodium or potassium hydroxide containing the indicator, or by using a solution of the hydroxide in a mixture of alcohol and water.

I claim:

1. An automated analytical method for determining the concentration of free fatty acids in a sample by titrating the fatty acids with a standard reagent solution of an alkali-metal hydroxide, the method comprising the steps of:

(a) calibrating and marking a container for a particular, predetermined, and specific weight of the sample with a first mark indicating the level to which the container is to be filled with the sample mixed with a solution of a visual acid-based indicator;

(b) calibrating and marking the container for a particular, predetermined, and specific volume of a standard reagent solution of an alkali-metal hydroxide having a concentration of from about one one-hundredth to about one gram equivalent weight per liter with a plurality of second marks disposed above the first mark, each of the second marks indicating the volume of the standard reagent solution required to reach the equivalence point of the titration and being so labeled as to be read directly and quantitatively as the percentage of free fatty acids in the sample, thereby automating the method;

(c) filling the container to the level indicated by the first mark with a liquid sample mixed with the solution of the acid-base indicator, wherein the temperature of the sample is from about 300° F. to about 350° F., thereby ensuring that the sample is a liquid and minimizing any inaccuracy due to the effect of temperature on the density and volume of the sample;

(d) titrating the free fatty acids present in the sample by slowly admixing the standard solution of alkali-metal hydroxide with the sample and the acid-base indicator solution present in the container until the equivalence point of the titration has been reached, as indicated by a change in color of the indictor; and (e) reading the percentage of free fatty acids in the sample directly from the second mark with indicates the volume of the standard reagent solution of alkali-metal hydroxide that was required to reach the equivalence point of the titration, without the necessity of any type of calculation.

2. An automated method for determining the concentration of free fatty acids in a sample of cooking fat or cooking oil, the method comprising the steps of:

(a) calibrating and marking a container for a particular, predetermined, and specific weight of the sample with a first mark indicating the level to which the container is to be filled with the sample of cooking fat or cooking oil;

(b) calibrating and marking the container for a particular, predetermined, and specific volume of an alcoholic solution of a visual acid-base indicator with a second mark disposed above the first mark;

(c) calibrating and marking the container for a particular, predetermined, and specific concentration of a standard solution of an alkali-metal hydroxide having a concentration of from about one one-hundredth to about one gram equivalent weight per liter with a plurality of third marks disposed above the second mark and so labeled as to be read directly and quantitatively as the percentage of free fatty acids in the sample, thereby automating the method;

(d) filling the container to the level indicated by the first mark with a liquid sample of the cooking fat or cooking oil at a temperature of from about 300° F. to about 350° F., thereby ensuring that the sample is a liquid and minimizing any inaccuracy due to the effect of temperature on the density and volume of the sample;

(e) admixing an alcoholic solution of a visual acid-base indicator to and with the sample up to the level indicated by the second mark;

(f) titrating the free fatty acids present in the sample by slowly admixing the standard solution of the alkali-metal hydroxide with the sample and the acid-base indicator solution present in the container until the equivalence point of the titration has been reached, as indicated by the change in color of the visual acid-base indicator; and (g) reading the percentage of free fatty acids in the cooking fat or cooking oil directly and quantitatively from the third mark with indicated the volume of the standard solution of the alkali-metal hydroxide required to reach the equivalence point of the titration, without the necessity of any type of calculation.

3. The method of claim 2, wherein the concentration of alkali-metal hydroxide is from about five one-hundredths to about five-tenths of a gram equivalent weight per liter, and the container is transparent.

* * * * *